(12) United States Patent
Sift et al.

(10) Patent No.: US 12,090,008 B2
(45) Date of Patent: Sep. 17, 2024

(54) ILLUMINATING INSTRUMENT FOR DIAGNOSTICS, SURGERY OR THERAPY

(71) Applicant: DENTSPLY SIRONA Inc., York, PA (US)

(72) Inventors: Michael Sift, Heddesheim (DE); Bernd Oehme, Mainz (DE); Alpdeniz Özer, Bensheim (DE)

(73) Assignee: DENTSPLY SIRONA INC., York, PA (US)

( * ) Notice: Subject to any disclaimer, the term of this patent is extended or adjusted under 35 U.S.C. 154(b) by 487 days.

(21) Appl. No.: 17/614,621

(22) PCT Filed: May 26, 2020

(86) PCT No.: PCT/EP2020/064495
§ 371 (c)(1),
(2) Date: Nov. 29, 2021

(87) PCT Pub. No.: WO2020/239719
PCT Pub. Date: Dec. 3, 2020

(65) Prior Publication Data
US 2022/0226071 A1   Jul. 21, 2022

(30) Foreign Application Priority Data

May 29, 2019   (EP) .................................. 19177390

(51) Int. Cl.
*A61C 1/08*   (2006.01)
*A61B 1/06*   (2006.01)
(Continued)

(52) U.S. Cl.
CPC ............ *A61C 1/088* (2013.01); *A61B 1/0607* (2013.01); *A61B 1/063* (2013.01); *A61B 1/0653* (2013.01);
(Continued)

(58) Field of Classification Search
CPC .......... A61B 1/07; A61B 1/0607; A61B 1/24; A61B 1/063; A61B 1/0653; A61B 1/0615;
(Continued)

(56) References Cited

U.S. PATENT DOCUMENTS 3,590,232 A * 6/1971 Sadowski ............ G02B 6/0005
433/29
6,607,384 B1 * 8/2003 Nakanishi ............. A61C 1/088
433/29
(Continued)

FOREIGN PATENT DOCUMENTS

DE   10209194 A1   10/2003
JP   H09-010227 A   1/1997
(Continued)

OTHER PUBLICATIONS

International Search Report; PCT/ EP2020/064495; Aug. 27, 2020 (completed); Sep. 10, 2020 (mailed).
(Continued)

*Primary Examiner* — Jacqueline T Johanas
*Assistant Examiner* — Shannel Nicole Belk
(74) *Attorney, Agent, or Firm* — DENTSPLY SIRONA INC.

(57) ABSTRACT

The present invention relates to an illuminating instrument (1) for diagnostics, therapy or surgery of a body part, comprising: at least one optical fiber (4) for transmitting electromagnetic radiation directly from an electromagnetic radiation source (3) to the body part; and a housing (5) which supports the optical fiber (4); the optical axis of the light-output end of the optical fiber (4) circumferentially extends in an illumination portion (52a) in the housing (5) which is annular shaped and arranged to face the body part; the optical fiber (4) in the illumination portion (52a) has one
(Continued)

or more diffusing regions (4a) for difusing the electromagnetic radiation to the outside of the optical fiber (4) through the circumferential surface (4b) thereof, a coupling device (2) which supports the electromagnetic radiation source (3) for generating the electromagnetic radiation, characterized by further comprising: a conversion means (6) which is supported by the housing (5) without directly contacting the electromagnetic radiation source (3), and arranged between the diffusing regions (4a) and the body part for converting the electromagnetic radiation into visible light for illuminating the body part, and wherein the light-entrance end of the optical fiber (4) is directly optically connected with the electromagnetic radiation source (3), wherein the conversion means (6) is outside an optical interface between the light-entrance end of the optical fiber (4) and the electromagnetic radiation source (3).

20 Claims, 5 Drawing Sheets

(51) Int. Cl.
  *A61B 1/07* (2006.01)
  *A61B 1/24* (2006.01)
  *A61C 3/02* (2006.01)
  *A61C 17/02* (2006.01)
(52) U.S. Cl.
  CPC .................. *A61B 1/07* (2013.01); *A61B 1/24* (2013.01); *A61C 3/02* (2013.01); *A61C 17/0202* (2013.01)
(58) Field of Classification Search
  CPC ......... A61B 1/0623; A61B 1/06; A61C 1/088; A61C 3/02; A61C 17/0202
  See application file for complete search history.

(56) References Cited

U.S. PATENT DOCUMENTS

| | | |
|---|---|---|
| 2006/0171693 A1 | 8/2006 | Todd |
| 2007/0121786 A1* | 5/2007 | Okawa ................. A61B 1/0615 378/65 |
| 2009/0040598 A1* | 2/2009 | Ito ........................ A61B 1/0638 359/332 |
| 2013/0137923 A1 | 5/2013 | Honda |
| 2014/0134568 A1* | 5/2014 | Heinrich ................. A61M 3/02 433/29 |
| 2016/0103312 A1 | 4/2016 | Furuta |
| 2018/0132970 A1 | 5/2018 | Ritter |

FOREIGN PATENT DOCUMENTS

| | | |
|---|---|---|
| JP | H09-140664 A | 6/1997 |
| JP | 3067847 U | 4/2000 |
| JP | 2005193012 A | 7/2005 |
| JP | 2006223688 A | 8/2006 |
| JP | 2013505084 A | 2/2013 |
| JP | 2013519774 A | 5/2013 |
| JP | 2014520640 A | 8/2014 |
| WO | 2002065937 A1 | 8/2002 |
| WO | 2012137737 A1 | 10/2012 |

OTHER PUBLICATIONS

International Preliminary Report on Patentability; PCT/ EP2020/ 064495; Aug. 27, 2020 (completed); Sep. 10, 2020 (mailed).
Written Opinion of the International Searching Authority; PCT/ EP2020/064495; Aug. 27, 2020 (completed); Sep. 10, 2020 (mailed).
Japanese Office Action dated Apr. 2, 2024.

* cited by examiner

ILLUMINATING INSTRUMENT FOR DIAGNOSTICS, SURGERY OR THERAPY

TECHNICAL FIELD OF THE INVENTION

The present invention relates to illuminating instruments for diagnostics, surgery or therapy. The present invention more particularly relates to an illuminating dental instrument for drilling, scaling, spraying or the like.

BACKGROUND ART OF THE INVENTION

A dental instrument for drilling, scaling or spraying generally needs an illumination for enabling the dentist to sufficiently clearly see the area being treated. Any sharp edges and color fringes in the illumination may lead to a fast fatigue of the dentist's eye. Furthermore, the shadows of the tool i.e., the drill, the scaler and the air/water jet can make it difficult for the dentist to work. Therefore, it is generally desired that a relatively large area can be intensively and uniformly illuminated. Due to its luminous efficiency, white LED technology is generally used for the illumination in dental instruments. Most white LEDs are manufactured as phosphor-conversion type LEDs which have a blue light emitting diode covered with yellow phosphor. The yellow phosphor emits white light upon excitation with the blue light. The LED technology is more efficient compared to incandescent lamps, however when used in environments where only a limited cooling is possible, the overheating leads to a reduction in the light output and the degradation of the LED.

DE10209194A1 discloses a handheld dental instrument for use with a detachable coupling device which has a light source for illuminating the object. This handheld dental instrument comprises an optical guide which is arranged to transmit the light from the light source to the body part. The light source is an LED with integrated phosphor. The handheld dental instrument has a housing which supports the optical guide. The housing is detachably attachable to the coupling device.

US 2014/0134568 A1 discloses a medical/dental instrument having a lighting device which has an LED with integrated phosphor in the head portion.

US 2007/0121786 A1 discloses a diagnostic/treatment instrument such as a handpiece with a dental instrument tool and a light radiating unit which has an LED with integrated phosphor.

DISCLOSURE OF THE INVENTION

An objective of the present invention is to overcome the disadvantages of the prior art and provide an illuminating instrument for diagnostics, surgery or therapy with an improved illumination.

This objective is achieved through the illuminating instrument for diagnostics, surgery or therapy as defined in claim 1. The subject-matters of the dependent claims relate to further developments.

The present invention provides an illuminating instrument for diagnostics, therapy or surgery of a body part. The illuminating instrument comprises at least one optical fiber for transmitting electromagnetic radiation from an electromagnetic radiation source to the body part; and a housing which supports the optical fiber. The optical axis of the optical fiber is circumferentially arranged in an illumination portion in the housing. The illumination portion is annular shaped and arranged to face the body part. The optical fiber in the illumination portion has one or more diffusing regions for diffusing the electromagnetic radiation to the outside of the optical fiber through the circumferential surface. The illuminating instrument further comprises a conversion means, preferably phosphor which is supported by the housing without directly contacting the electromagnetic radiation source and arranged between the diffusing regions and the body part for converting the electromagnetic radiation into visible light for illuminating the body part. The conversion means is outside the optical interface between the optical fiber and the electromagnetic radiation source.

A major advantageous effect of the present invention is that a relatively large area can be intensely and uniformly illuminated without any shadows by the diffusing regions through the circumferential surface of the optical fiber which is circumferentially arranged in the annular shaped illumination portion of the illuminating instrument. Another major advantageous effect of the present invention is that the electromagnetic radiation source is prevented from overheating as the conversion means is arranged away from the electromagnetic radiation source, namely on the light exit side which is exposed by the diffusing regions. Thereby, a temperature dependent color shift in the illumination can be prevented. Thereby also the radiation output of the electromagnetic radiation source can be generally increased, and the illumination efficiency can be improved. The life of the electromagnetic radiation source can be prolonged, and the need for maintenance can be obviated or reduced. Since the overheating is suppressed, the electromagnetic radiation source may be safely operated even at higher radiation output levels to attain a more intense illumination. Furthermore, due to the suppression of the overheating, the illuminating instrument can be more safely and comfortably held by the user during the applications. For instance, the user's hand can be prevented from sweating.

According to an embodiment of the present invention, the illuminating instrument is preferably adapted for use with a coupling device which has an electromagnetic radiation source, for instance an LED or a laser diode without a conversion means such as phosphor or the like. The coupling device is preferably detachably attachable to the housing. Alternatively, the coupling device may be an integral part of the illuminating instrument. The coupling device preferably has a hose including at least an electric wiring for connection to an electric power supply for powering the electromagnetic radiation source. In this embodiment, the coupling device and the illuminating instrument constitute an illuminating system. Alternatively, the coupling device may be battery driven. The battery may be exchangeable and/or rechargeable through a charging adapter. Alternatively, the hose of the coupling device may have another optical fiber for transmitting the electromagnetic radiation to the illuminating instrument.

According to an embodiment of the present invention, the diffusing region preferably has a size and shape which matches the geometry of the area to be illuminated. The diffusing region preferably extends over the entire illumination portion. Alternatively, a plurality of identical diffusing regions are arranged at regular separations along the annular shaped illumination portion. Alternatively, the diffusing regions may be arranged at irregular separations along the annular shaped illumination portion.

According to an embodiment of the present invention, the optical fiber is preferably arranged into a groove which is formed into the surface of the housing. The groove is preferably provided in a size and shape that matches the optical fiber. The cross section of the groove is preferably parabolic to attain uniform illumination towards the body part. However, the groove may have various cross sections. For instance, the cross section is alternatively u-shaped. The depth of the groove is preferably slightly larger than the diameter of the optical fiber to provide space for filling a translucent sealing substance which has preferably a light diffusing characteristic.

According to an embodiment of the present invention, the illumination portion preferably has a reflective surface to reflect the light towards the body part. The reflective surface is obtained by polishing the groove. Alternatively, the groove may be coated with a reflective substance. Alternatively, a separate annular shaped optical reflective surface is arranged into the groove behind the optical fiber.

According to an embodiment of the present invention, one or more lenses are preferably arranged between the diffusing regions and the body part respectively. The lens is preferably annular shaped. Thereby the size and shape of the illumination can be adjusted to the application.

According to alternative embodiments of the present invention, the illuminating instrument is preferably provided with a dental device such as dental spray device, a dental drill device, or a dental scaler device, or a camera for medical imaging. The camera may be sensitive to visible light, UV light or IR light. In these embodiments, the hose of the coupling device is preferably provided, in addition to the electric wiring, with supply lines for pressurized air and/or pressurized liquid. The dental spray device has nozzles for ejecting the pressurized air and the pressurized liquid. The dental drill device has a hub and a drill supported by the hub. The dental drill device is preferably driven by a turbine. Alternatively, an electric motor may be used. The dental scaler device has a tip for scaling. The housing preferably has a grip portion and a head portion for supporting the respective dental device and/or the camera. The annular-shaped illumination portion is in the head portion around the camera, the nozzles, or the drill or the scaling tip to attain shadowless uniform illumination.

According to an embodiment of the present invention, the optical fiber preferably extends, inside the housing, from the grip portion to the illumination portion in the head portion.

According to an embodiment of the present invention, the diffusion region of the optical fiber preferably has at least a structure adapted to scatter the electromagnetic radiation to the outside. The structure includes voids and/or particles formed in the optical fiber. The structures are preferably formed into the core and/or the cladding of the optical fiber. The optical fiber in the illumination portion is provided without any protective coatings to enable the diffusion of the electromagnetic radiation through the circumferential surface.

According to alternative embodiments of the present invention, the electromagnetic radiation source is preferably adapted to user selectively emit blue light, violet light, or infrared light. The conversion means has a conversion material, preferably phosphor and/or lanthanide doped nanoparticles. The lanthanide doped nanoparticles convert near infrared light into near ultraviolet light which can be used for bioimaging. The conversion material is preferably coated onto the optical fiber at the respective diffusing region. Alternatively, the conversions material is arranged near the respective diffusing region. Different diffusing regions may have different compositions of the conversion material for illumination and/or medical imaging.

BRIEF DESCRIPTION OF THE DRAWINGS

In the subsequent description, the present invention will be described in more detail by using exemplary embodiments and by referring to the drawings, wherein FIG. 1—is a schematic perspective view of an illuminating system having the illuminating instrument and the coupling device according to an embodiment of the present invention.

Figure 1:
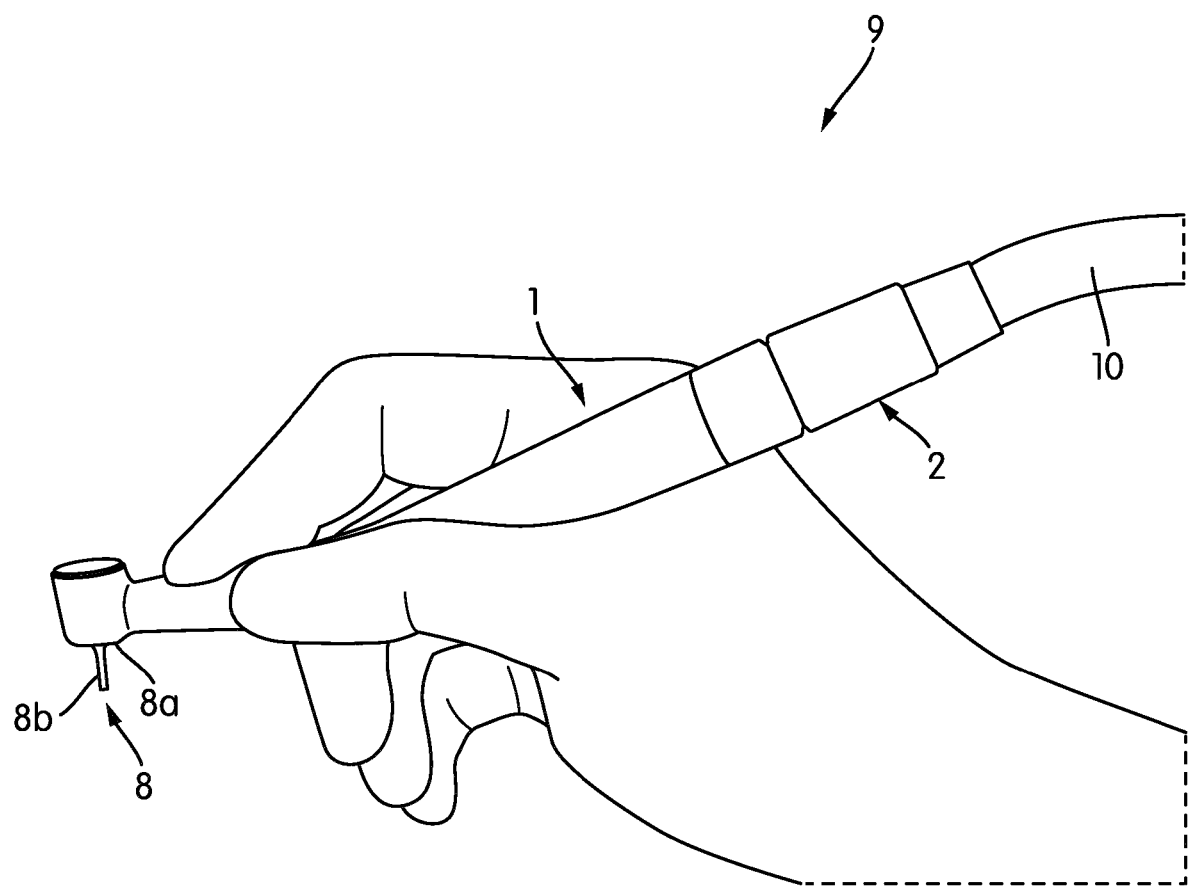

The reference numbers shown in the drawings denote the elements as listed below and will be referred to in the subsequent description of the exemplary embodiments.

| | | |
|---|---|---|
| 1. | Illuminating instrument | |
| 2. | Coupling device | |
| 3. | E.M. Radiation source | |
| 4. | Optical fiber | |
| | 4a. | Diffusing regions |
| | 4b. | Circumferential surface |
| 5. | Housing | |
| | 51. | Grip portion |
| | 52. | Head portion |
| | 52a. | Illumination portion |
| | 52b. | Groove |
| 6. | Conversion means | |
| | 6a. | Conversion material |
| 7. | Reflective surface | |
| 8. | Dental drill device | |
| | 8a. | Hub |
| | 8b. | Drill |
| 9. | Illuminating system | |
| 10. | Hose | |
| 11. | Lens | |
| 12. | Diffusor | |

Figure 2A:
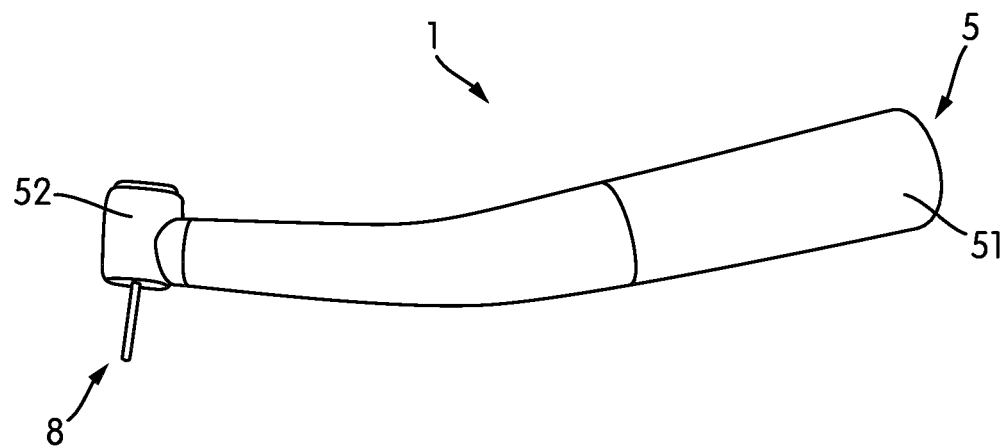
FIG. 2A—is a schematic perspective view of the illuminating instrument in FIG. 1.
Figure 2B:
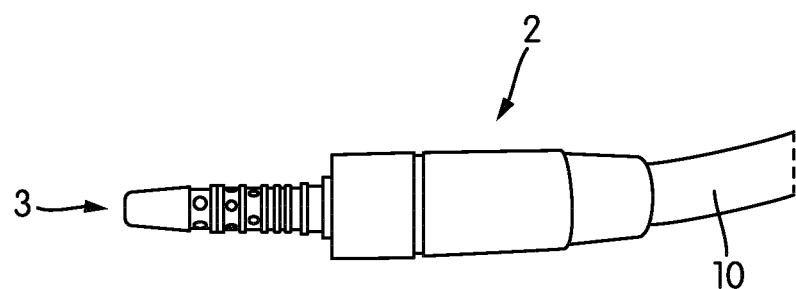
FIG. 2B—is a schematic perspective view of the coupling device in FIG. 1.
Figure 3:
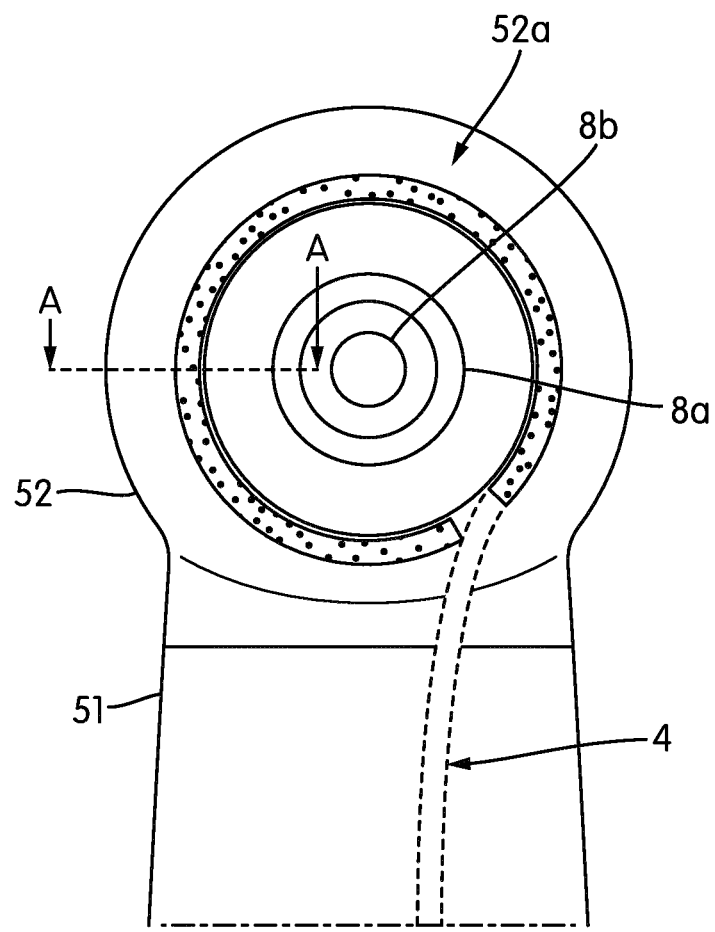
FIG. 3—is a schematic bottom view of the head portion of the illuminating instrument in FIG. 1.
Figure 4A:
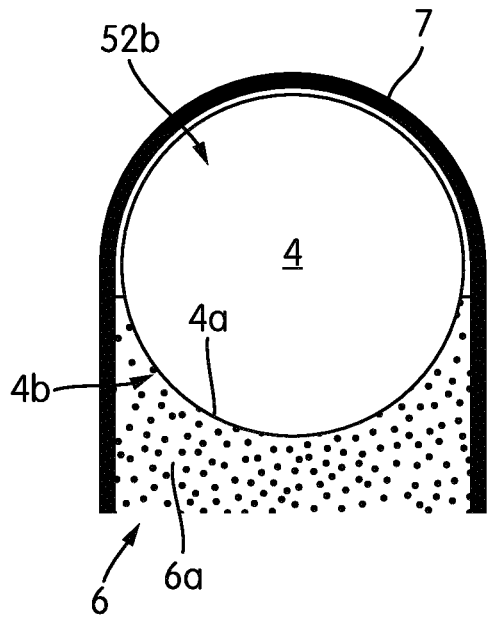
FIG. 4A—is a schematic cross sectional view of the head portion of the illuminating instrument in FIG. 1, taken along the line A-A in FIG. 3.
Figure 4B:
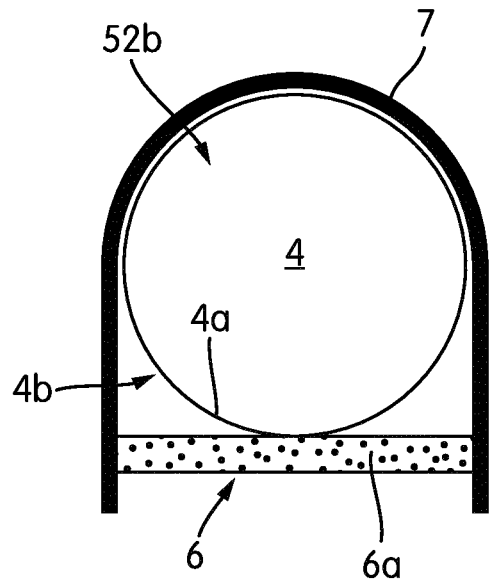
FIG. 4B—is a schematic cross sectional view of the head portion of the illuminating instrument according to another embodiment, taken along the line A-A in FIG. 3.
Figure 4C:
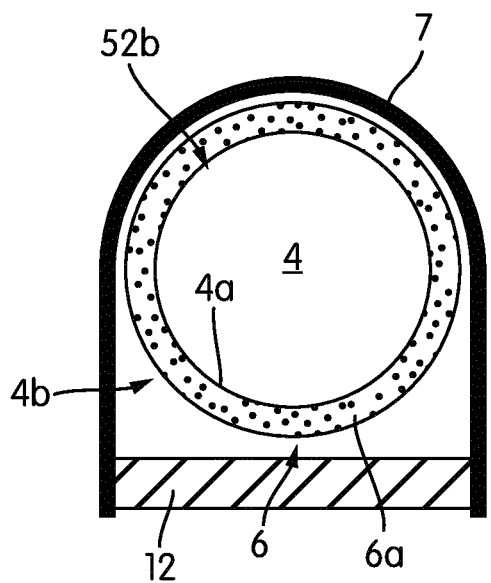
FIG. 4C—is a schematic cross sectional view of the head portion of the illuminating instrument according to another embodiment, taken along the line A-A in FIG. 3.
Figure 4D:
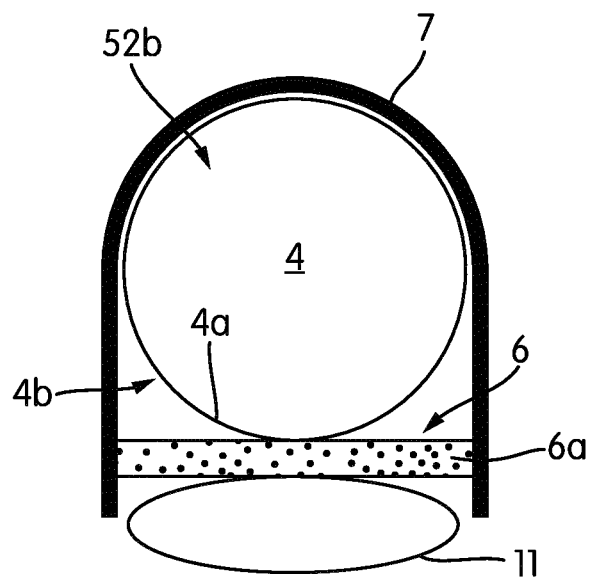
FIG. 4D—is a schematic cross sectional view of the head portion of the illuminating instrument according to another embodiment, taken along the line A-A in FIG. 3.
Figure 5:
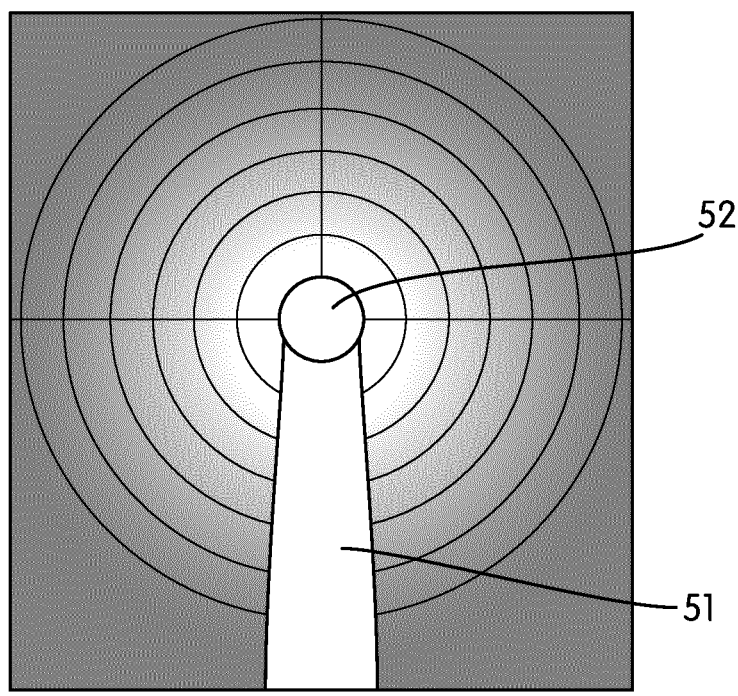
FIG. 5—is a schematic partial top view of the illuminating instrument showing the light distribution of the illumination.

FIG. 1 shows an illuminating system (9) according to an embodiment of the present invention. As shown in FIG. 2A and FIG. 2B, the illuminating system (9) has an illuminating instrument (1) and a coupling device (2). The illuminating instrument (1) is suitable for diagnostics, therapy or surgery of a body part. The illuminating instrument (1) is adapted for use with the coupling device (2). As shown in FIG. 2A and FIG. 2B, the illuminating instrument (1) and the coupling device (2) are detachably attachable. The housing (5) of the illuminating instrument (1) can be detachably attached to the coupling device (2). Alternatively, the coupling device (2) may fixed to the housing (5) so that it cannot be detached by the user. As shown in FIG. 2B, the coupling device (2) has an electromagnetic radiation source (3) for generating electromagnetic radiation. The electromagnetic radiation source (3) is preferably a LED without an integrated phosphor element that directly contacts the semiconductor. The coupling device (2) has a hose (10) for supplying electric power to the electromagnetic radiation source (3). As shown in FIG. 2A and FIG. 3, the housing (5) has a grip portion (51) and a head portion (52). As shown in FIG. 3, the head portion (52) has an illumination portion (52a). The illuminating instrument (1) has an optical fiber (4) for transmitting the electromagnetic radiation from the electromagnetic radiation source (3) to the illumination portion (52a) which faces the body part. As shown in FIG. 3, the optical fiber (4) is single-piece and has a light-output end and a light entrance end. Thereby the loss of illumination can be reduced as much as possible. The light-output end is in the head portion (52) and the light entrance end is in the grip portion (51). Alternatively, the optical fiber (4) may have exactly two pieces wherein one piece may have the light-output end which is in the head portion (52), and wherein the second piece may have the light entrance end which is in the grip portion (51). Thereby the assembly process can be simplified. These two-pieces can be connected during the assembly of the grip portion (51) and the head portion (52). The optical fiber (4) is supported by the housing (5) of the illuminating instrument (1). The optical fiber (4) extends, inside the housing (5), from the grip portion (51) to the illumination portion (52a) of the head portion (52). As shown in FIG. 3, the optical axis of the light-output end of the optical fiber (4) circumferentially extends in the illumination portion (52a) of the housing (5). The illumination portion (52a) is annular shaped and arranged to face the body part. FIG. 4A shows the cross section of the illumination portion (52a) of the illuminating instrument (1) in FIG. 1, taken along the line A-A in FIG. 3. The illumination portion (52a) has a groove (52b) on the surface of the housing (5). The optical axis of the light-output end of the optical fiber (4) is circumferentially arranged in the groove (52b). The groove (52b) matches the shape of the light output end of the optical fiber (4). As shown in FIG. 4A, the optical fiber (4) in the illumination portion (52a) has a diffusing region (4a) for diffusing the electromagnetic radiation to the outside of the optical fiber (4) through the circumferential surface (4b). The light-entrance end of the optical fiber (4) is directly connected/coupled with the electromagnetic radiation source (3). The diffusing region (4a) is annular shaped and extends over the complete illumination portion (52a). The illumination portion (52a) has a reflecting surface (7). The diffusion region (4a) of the optical fiber (4) has a structure adapted to scatter the electromagnetic radiation to the outside. The structure comprises voids and particles. The electromagnetic radiation source (3) is an LED which is adapted to emit blue light. The blue light emitting LED has no phosphor coating to prevent overheating inside the grip portion (51). Alternatively, an LED which emits violet light may be used. As shown in FIG. 4A, a conversion means (6) is supported by the housing (5) and arranged between the diffusing region (4a) and the body part for converting the electromagnetic radiation into visible light for illuminating the body part. As shown in FIG. 4A, the conversions means (6) has a conversion material (6a) that is directly arranged onto the respective diffusing region (4a). The conversion material (6a) includes phosphor. FIG. 4B to FIG. 4C show alternative versions of the embodiment. As shown in FIG. 4B and FIG. 4D, the conversion material (6a) is arranged as a thick layer on the respective diffusing region (4a). As shown in FIG. 4C, the conversion material (6a) is coated on the diffusing region (4a). As shown in 4C, an additional diffusor (12) is arranged between the diffusing region (4a) and the body part. As shown in 4D, a lens (11) is arranged between the diffusing region (4a) and the body part. The gaps in the groove (52b) are filled with a heat resistant transparent sealing material. As shown in FIG. 1, the illuminating instrument (1) has a dental drill device (8). The dental drill device (8) has a hub (8a) and a drill (8b) supported by the hub (8a). The head portion (52) supports the hub (8a). As shown in FIG. 3, the illumination portion (52a) is in the head portion (52) around the hub (8a). Alternatively, the illuminating instrument (1) may be provided with a dental spray device, a dental scaler device, and/or a camera. The camera may be detachably attachable to the outside of the housing (5) through a retainer on the housing (5). The retainer may be integrated or detachable as well. The camera is arranged to view the illuminated region underside head portion (52). From the acquired images the alignment/position of the illuminating instrument (1), specifically the dental drill, the scaler, the nozzle can be determined, and thus the user can be provided with a feedback for guidance based on the planned handling. The camera is preferably a 2D or 3D camera.

The invention claimed is:

1. An illuminating instrument (1) for diagnostics, therapy or surgery of a body part, comprising:
   at least one optical fiber (4) for transmitting electromagnetic radiation directly from an electromagnetic radiation source (3) to the body part; and
   a housing (5) which supports the optical fiber (4);
   the optical axis of the light-output end of the optical fiber (4) circumferentially extends in an illumination portion (52a) in the housing (5) which is annular shaped and arranged to face the body part;
   the optical fiber (4) in the illumination portion (52a) has one or more diffusing regions (4a) for diffusing the electromagnetic radiation to the outside of the optical fiber (4) through the circumferential surface (4b) thereof,
   a coupling device (2) which supports the electromagnetic radiation source (3) for generating the electromagnetic radiation,
   characterized by further comprising:
   a conversion means (6) which is supported by the housing (5) without directly contacting the electromagnetic radiation source (3), and arranged between the diffusing regions (4a) and the body part for converting the electromagnetic radiation into visible light for illuminating the body part, and
   wherein the light-entrance end of the optical fiber (4) is directly optically connected with the electromagnetic radiation source (3), wherein the conversion means (6) is outside an optical interface between the light-entrance end of the optical fiber (4) and the electromagnetic radiation source (3).

2. The illuminating instrument (1) according to claim 1, characterized in that the coupling device (2) is detachably attachable to the housing (5).

3. The illuminating instrument (1) according to claim 2, characterized in that the housing (5) has a grip portion (51) and a head portion (52), wherein the illumination portion (52a) is in the head portion (52), wherein the coupling device (2) is detachably attachable to grip portion (51).

4. The illuminating instrument (1) according to claim 3, characterized in that the optical fiber (4) extending between the light-output end and the light-entrance end is a single-piece optical fiber (4), wherein the conversion means (6) and the light-output end are in the head portion (52), and wherein the light entrance end is in the grip portion (51).

5. The illuminating instrument (1) according to claim 1, characterized in that the diffusing region (4a) is also annular shaped and extends over the complete illumination portion (52a) so as to produce an annular-shaped illumination.

6. The illuminating instrument (1) according to claim 1, characterized in that the illumination portion (52a) comprises a groove (52b) on the surface of the housing (5), wherein the groove (52b) matches the shape of the optical fiber (4).

7. The illuminating instrument (1) according to claim 1, characterized in that the illumination portion (52a) comprises a reflecting surface (7).

8. The illuminating instrument (1) according to claim 1, characterized by further comprising one or more lenses (II) arranged between the diffusing regions (4a) and the body part respectively.

9. The illuminating instrument (1) according to claim 1, characterized by further comprising a dental spray device having one or more nozzles, wherein the housing (5) has a grip portion (51) and a head portion (52) for supporting the dental spray device, and wherein the illumination portion (52a) is in the head portion (52) around the nozzles of the dental spray device.

10. The illuminating instrument (1) according to claim 1, characterized by further comprising a dental drill device (8) having a hub (8a) and a drill (8b) supported by the hub (8a), wherein the housing (5) has a grip portion (51) and a head portion (52) for supporting the hub (8a), wherein the illumination portion (52a) is in the head portion (52) around the hub (8a).

11. The illuminating instrument (1) according to claim 1, characterized by further comprising a dental scaler device having a tip, wherein the housing (5) has a grip portion (51) and a head portion (52) for supporting the tip, wherein the illumination portion (52a) is in the head portion (52) around the tip.

12. The illuminating instrument (1) according to claim 1, characterized in that the optical fiber (4) extends, inside the housing (5), from the grip portion (51) to the illumination portion (52a) of the head portion (52).

13. The illuminating instrument (1) according claim 1, characterized in that one or more diffusion regions (4a) of the optical fiber (4) each has at least a structure adapted to scatter the electromagnetic radiation to the outside, wherein the structure comprises voids and/or particles.

14. The illuminating instrument (1) according to claim 1, characterized in that the electromagnetic radiation source (3) is adapted to emit blue light.

15. The illuminating instrument (1) according to claim 1, characterized in that the electromagnetic radiation source (3) is adapted to emit violet light.

16. The illuminating instrument (1) according to claim 1, characterized in that the electromagnetic radiation source (3) is adapted to emit infrared light.

17. The illuminating instrument (1) according to claim 1, characterized in that the conversions means (6) comprises conversion material (6a) that is coated onto the respective diffusing region (4a) or arranged separately in close proximity of the respective diffusing region (4a).

18. The illuminating instrument (1) according to claim 17, characterized in that the conversion material (6a) comprises phosphor and/or lanthanide doped nanoparticles.

19. The illuminating instrument (1) according to claim 1, characterized by further comprising: a hose (10) for supplying the coupling device (2) at least with electric power.

20. The illuminating instrument (1) according to claim 1, characterized by further comprising: a camera which is arranged to view the illuminated region by the illumination portion (52a).

* * * * *